United States Patent
Brand et al.

(10) Patent No.: US 8,927,040 B2
(45) Date of Patent: Jan. 6, 2015

(54) EXTRACTION DEVICE AND METHOD FOR EXTRACTING INGREDIENTS FROM A BIOLOGICAL SAMPLE

(75) Inventors: Wolfgang Brand, Venningen (DE); Karl Henn, Schwetzingen (DE); Sven Mahler, Ludwigshafen (DE); Ralf Looser, Berlin (DE)

(73) Assignee: BASF Plant Science Company GmbH, Ludwigshafen (DE)

( * ) Notice: Subject to any disclaimer, the term of this patent is extended or adjusted under 35 U.S.C. 154(b) by 0 days.

(21) Appl. No.: 13/823,421
(22) PCT Filed: Sep. 15, 2011
(86) PCT No.: PCT/EP2011/066044
§ 371 (c)(1),
(2), (4) Date: Mar. 14, 2013
(87) PCT Pub. No.: WO2012/035117
PCT Pub. Date: Mar. 22, 2012

(65) Prior Publication Data
US 2013/0171629 A1 Jul. 4, 2013

Related U.S. Application Data

(60) Provisional application No. 61/382,940, filed on Sep. 15, 2010.

(30) Foreign Application Priority Data

Sep. 15, 2010 (EP) .................................. 10176888

(51) Int. Cl.
*A23L 1/28* (2006.01)
(Continued)

(52) U.S. Cl.
CPC .......... *G01N 1/34* (2013.01); *G01N 2001/4061* (2013.01); *B01D 11/0219* (2013.01);
(Continued)

(58) Field of Classification Search
USPC ............ 424/725; 426/425, 431, 481; 435/6.1, 435/283.1, 287.2
See application file for complete search history.

(56) References Cited

U.S. PATENT DOCUMENTS 4,744,926 A * 5/1988 Rice ................................. 554/8
5,382,414 A 1/1995 Lautenschlager
(Continued)

FOREIGN PATENT DOCUMENTS

EP 0446970 A2 9/1991
EP 1820549 A2 8/2007
(Continued)

OTHER PUBLICATIONS

International Search Report for PCT/EP2011/066044, mailed Oct. 25, 2011.
(Continued)

*Primary Examiner* — Narayan Bhat
(74) *Attorney, Agent, or Firm* — Drinker Biddle & Reath LLP (57) ABSTRACT

An extraction device (110) for extracting at least one ingredient from a biological sample (112) is disclosed, specifically for extracting metabolites from a plant specimen. The extraction device (110) has at least one liquid charger (116) which is adapted to be brought in contact with a first side (122) of the sample (112). The liquid charger (116) is adapted to apply an extraction liquid (128), specifically at least one solvent, to the first side (122) of the sample (112). The extraction device (110) further has at least one sampling device (118) which is adapted to be brought in contact with a second side (124) of the sample (112). The sampling device (118) is adapted to collect sample fluid (126) comprising the extraction liquid (128) and the ingredient.

28 Claims, 2 Drawing Sheets

(51) Int. Cl.
*A23L 1/20* (2006.01)
*A23L 1/10* (2006.01)
*A01N 65/00* (2009.01)
*C12Q 1/68* (2006.01)
*C12M 1/00* (2006.01)
*B01D 11/02* (2006.01)
*G01N 1/34* (2006.01)
*G01N 1/40* (2006.01)

(52) U.S. Cl.
CPC .................................. *G01N 1/4055* (2013.01)
USPC ........... 426/425; 426/431; 426/481; 424/725; 435/6.1; 435/283.1

(56) References Cited

U.S. PATENT DOCUMENTS

| | | |
|---|---|---|
| 5,447,077 A | 9/1995 | Lautenschlager |
| 5,529,694 A | 6/1996 | Strickler |
| 5,716,525 A | 2/1998 | Nickerson |
| 2002/0000410 A1* | 1/2002 | Kim et al. ...................... 210/634 |
| 2002/0197631 A1* | 12/2002 | Lawrence et al. .................. 435/6 |
| 2006/0057738 A1* | 3/2006 | Hall, Jr. ........................ 436/177 |
| 2007/0183999 A1 | 8/2007 | Grollier et al. |
| 2009/0142837 A1* | 6/2009 | Adams et al. .................. 435/441 |
| 2010/0089132 A1 | 4/2010 | Larter et al. |
| 2011/0272353 A1 | 11/2011 | Herold et al. |

FOREIGN PATENT DOCUMENTS

| | | |
|---|---|---|
| EP | 1446209 B1 | 3/2008 |
| EP | 2330402 A1 | 6/2011 |
| WO | WO-00/54023 A1 | 9/2000 |

OTHER PUBLICATIONS

International Preliminary Report on Patentability for PCT/EP2011/066044, dated Oct. 11, 2012.

* cited by examiner

EXTRACTION DEVICE AND METHOD FOR EXTRACTING INGREDIENTS FROM A BIOLOGICAL SAMPLE

RELATED APPLICATIONS

This application is a national stage application (under 35 U.S.C. §371) of PCT/EP2011/066044, filed Sep. 15, 2011, which claims benefit of European Application No. 10176888.5, filed Sep. 15, 2010, and U.S. Provisional Application No. 61/382,940, filed Sep. 15, 2010.

FIELD OF THE INVENTION

The invention relates to an extraction device and a method for extracting at least one ingredient from a biological sample. The invention further relates to an extraction system, comprising an extraction device and a biological sample. Extraction devices, extraction systems and methods according to the invention may preferably be used in the field of development of plants, such as the development of transgenic plant lines as well as in the field of development of compounds and methods for a treatment of plants and plant entities, such as the development of fertilizers, pesticides, herbicides, growth enhancers and other compounds. The invention may further be used for detecting potential effects of one or more external influences on certain plants and/or for detecting potential effects of certain plants or parts of plants, such as toxicological or pharmaceutical effects. Moreover, the invention may be used in the field of plant biotechnology such as for the development of transgenic plant lines and in the field of plant breeding.

RELATED ART

In the field of plant biology, development of pesticides and fertilizers as well as in the field of toxicology, assessments of biochemical ingredients of plants and specifically investigations of the plant's metabolism have become a widely used tool. Thus, specifically in the field of development of treatments for certain plants and plant entities, the plant's metabolism and specifically certain metabolites being used as markers, may provide important insights into the plant's reaction to these treatments, in addition or alternatively to simply watching the plant's exterior signals, such as color, plant growth, plant volume or root volume. Similarly in the field of plant breeding or the characterization and development of transgenic plant lines for crop improvement the plant's metabolism may provide important insights into the plant's development or performance potential, in addition or alternatively to simply watching the plant's growth, development or phenotype including the final yield. Thus, by assessing certain metabolite markers, it may even be possible to predict the plant's development and/or reaction long before exterior signs like phenotypic changes are available. Further, by comparing e.g. the decrease or increase of certain metabolite markers with the decrease or increase of metabolites in other, known treatments, the effect e.g. the development or the performance of the plant of a treatment in question, such as a treatment with a certain chemical compound, may be predicted. By grouping certain metabolite reactions, treatments may be clustered, and new treatments having a similar effect may be found by simply searching for similar metabolite patterns.

For all these investigations, reliable devices and methods for extracting metabolites from the plant samples are required. Commonly, a plant sample is taken, such as a sample from the plant's leaf, by dissecting the sample from the plant's body. The sample is disintegrated in a suitable vessel, e.g. by milling, mashing or other techniques suited to disintegrate the sample's outer structure. One or more solvents are added to dissolve the plant's ingredients that are to be extracted. Finally, the solvents containing the one or more ingredients are separated from the sample, such as by filtering and/or centrifugation methods. These solvents, containing the one or more ingredients, may further be evaluated by typical analytical methods, such as by spectroscopic methods, chemical analysis, mass spectroscopy, gas chromatography, liquid chromatography or combinations of the named methods.

These known methods for extracting one or more ingredients from the sample are, however, disadvantageous and detrimental to the sample in several ways. Thus, the sample preparation is rather time-consuming, leaving enough time for sample components to alter, such as by oxidation or other chemical reactions. Further, dissecting the sample from the remaining plant may change the plant sample itself, such as by exerting stress onto the plant, and, thus, may potentially falsify the results of the metabolite reactions.

Problem to be Solved

It is therefore an objective of the present invention to provide devices and methods for extracting at least one ingredient from a biological sample, which at least partially avoid the disadvantages of known devices and methods. Specifically, a fast and reliable way of extraction should be provided, without time-consuming sample preparation, having a minimum impact on the sample and/or remaining biological entity itself.

Disclosure of the Invention

This problem is solved by an extraction device and a method for extracting at least one ingredient from a biological sample, in accordance with the independent claims. Preferred embodiments of the invention, which may be realized alone or in combination with one or more of the other preferred embodiments, are disclosed in the dependent claims.

In the following, the terms "have", "contain" and "comprise" as well as grammatical variations thereof are used in a non-exclusive way. Thus, the expressions "A has B", "A contains B" and "A comprises B" may both imply the case in which A solely consists of B without having any further components or constituents and the case in which A, besides B, contains one or more further components or constituents.

In a first aspect of the present invention, an extraction device for extracting at least one ingredient from a biological sample is disclosed. As used in this disclosure, an extraction device may comprise any apparatus or a combination of apparatuses, which are suited for extracting the at least one ingredient, preferably by using one or more liquid and/or gaseous solvents.

The term "biological sample" as used herein may preferably refer to samples comprising biological material from all biological sources. It will be understood that the biological material shall comprise metabolites.

The biological sample may comprise any sample that may be taken from a living being or entity, preferably a sample which may be taken from a plant. The biological sample preferably may comprise living cells. The sample preferably may comprise an entire or whole part of the living being or living entity, such as a self-supporting part of the living being or living entity, preferably without the need of providing a carrier element. Thus, the biological sample preferably may consist solely of the part of the living being or living entity. As a preferred embodiment, the part of the living being or living entity directly is taken from the living being or living entity, as an intact part, without any further steps of conditioning or processing. As used herein, the terms "conditioning" and processing specifically may be understood as a means of preserving the biological sample by e.g. freezing or freeze drying the biological sample prior to the extraction of the ingredient(s) from the biological sample using the extraction device. Thus, preferably, the biological sample may be taken from a plant and may be subject to an extraction process by using the extraction device according to the present invention and/or the extraction method according to the present invention, without any intermediate step of freezing or freeze drying biological sample prior to the extraction of the at least one ingredient.

In a further embodiment, the part of the living being or living entity, directly taken from the living being or living entity, may still be subject to propagation via tissue culture. Preferably, the biological sample, at least at the beginning of the extraction process of the at least one ingredient, still is living or contains living matter such as living cells. Thus, preferably, at least at the beginning of the extraction process of the at least one ingredient, it may still be possible to reproduce the biological sample or parts thereof, such as by breeding of cell cultures and/or tissue cultures taken from the biological sample.

The part of the living being may be subject to further manipulations prior to the extraction of the at least one ingredient from the biological sample by using the extraction device. More preferably, the size of the part of the living being may be adjusted to the measures of the extraction device prior extraction. Thus, specifically, the size and/or dimensions of the biological sample may be adapted to the extraction device, such as to the dimensions of a sample space of the extraction device in between the liquid charger and the sampling device. For adapting the size and/or the dimensions of the biological sample, any known method may be used, such as a cutting process.

As non-limiting examples, leaves, trunks, stems, roots, storage roots, branches, inflorescences, flowers, infructescences, fruits, ears, cobs, seeds or other samples taken from a plant may be named.

In a preferred embodiment the biological sample may be or may comprise an intact part of a plant growing in a controlled environment like a growth chamber or a greenhouse.

In another preferred embodiment the biological sample may be or may comprise an intact part of a plant growing in soil or in a hydroponic system in a controlled environment like a growth chamber or a greenhouse.

In another preferred embodiment the biological sample may be or may comprise an intact part of a plant growing in a field. The field may either be a test field, where plants are grown under specific growing regimes imposing abiotic or biotic stress to the plants in order to monitor their reaction or performance, or a usual field where plants are grown by farmers to later harvest them.

In another preferred embodiment the biological sample may be or may comprise an intact part of a plant, which belongs to a breeding population.

In another preferred embodiment the biological sample may be or may comprise an intact part of a plant, which belongs to a transgenic plant.

The term "plant" as used herein may refer to a wide variety of monocotyledonous or dicotyledonous plants, preferably plants like maize, wheat, rye, oat, triticale, rice, barley, sorghum, sugar cane, soybean, peanut, cotton, rapeseed and canola, manihot, pepper, sunflower and tagetes, sugar beet, solanaceous plants like potato, tobacco, eggplant, and tomato, Vicia species, pea, alfalfa, bushy plants (coffee, cacao, tea), Salix species, trees (oil palm, coconut), perennial grasses, and forage crops. Forage crops include, but are not limited to Wheatgrass, Canarygrass, Bromegrass, Wildrye Grass, Bluegrass, Orchardgrass, Alfalfa, Salfoin, Birdsfoot Trefoil, Alsike Clover, Red Clover and Sweet Clover. More preferably the "plant" as used herein refers to rice, soybean, maize, cotton, canola, wheat, sugar beet and sugarcane.

The at least one ingredient may comprise any component which may be present in the biological sample. Preferably, the at least one ingredient may comprise one or more metabolites. Thus, preferably, the extraction device may be used or may be suited for extracting one or more metabolites from a plant specimen, preferably selectively, preferably with a high selectivity.

The term "metabolites" as used herein refers to small molecule compounds, such as substrates for enzymes of metabolic pathways, intermediates of such pathways or the products obtained by a metabolic pathway. Metabolic pathways are well known in the art and may vary between species. Preferably, said pathways include at least citric acid cycle, respiratory chain, photosynthesis, photorespiration, glycolysis, gluconeogenesis, hexose monophosphate pathway, oxidative pentose phosphate pathway, reductive pentose phosphate pathway, production and β-oxidation of fatty acids, urea cycle, amino acid biosynthesis pathways, protein degradation pathways such as proteasomal degradation, amino acid degrading pathways, biosynthesis or degradation of: lipids, polyketides (including e.g. flavonoids and isoflavonoids), isoprenoids (including eg. terpenes, sterols, steroids, carotenoids, xanthophylls), carbohydrates, phenylpropanoids and derivatives, alcaloids, benzenoids, indoles, indole-sulfur compounds, porphyrines, anthocyans, hormones such as phytohormones, vitamins, cofactors such as prosthetic groups or electron carriers, lignin, glucosinolates, purines, pyrimidines, nucleosides, nucleotides and related molecules such as tRNAs, microRNAs (miRNA) or mRNAs. Accordingly, small molecule compound metabolites are preferably composed of the following classes of compounds: alcohols, alkanes, alkenes, alkines, aromatic compounds, ketones, aldehydes, carboxylic acids, esters, amines, mines, amides, cyanides, amino acids, peptides, thiols, thioesters, phosphate esters, sulfate esters, thioethers, sulfoxides, ethers, or combinations or derivatives of the aforementioned compounds. The small molecules among the metabolites may be primary metabolites which are required for normal cellular function, organ function or plant growth, development or health. Moreover, small molecule metabolites further comprise secondary metabolites having essential ecological function, e.g. metabolites which allow an organism to adapt to its environment. Furthermore, metabolites are not limited to said primary and secondary metabolites and further encompass artificial small molecule compounds. Said artificial small molecule compounds are derived from exogenously provided small molecules which are administered or taken up by an organism but are not primary or secondary metabolites as defined above. For instance, artificial small molecule compounds may be metabolic products obtained from a wide range of variety of compounds such as from fertilizers, pesticides, herbicides or growth enhancers, by metabolic pathways of the plant. Moreover, metabolites further include peptides, oligopeptides, polypeptides, oligonucleotides and polynucleotides, such as RNA or DNA. More preferably, a metabolite has a molecular weight of 50 Da (Dalton) to 30,000 Da, most preferably less than 30,000 Da, less than 20,000 Da, less than 15,000 Da, less than 10,000 Da, less than 8,000 Da, less than 7,000 Da, less than 6,000 Da, less than 5,000 Da, less than 4,000 Da, less than 3,000 Da, less than 2,000 Da, less than 1,000 Da, less than 500 Da, less than 300 Da, less than 200 Da, less than 100 Da. Preferably, a metabolite has, however, a molecular weight of at least 50 Da. Most preferably, a metabolite in accordance with the present invention has a molecular weight of 50 Da up to 1,500 Da.

The extraction device has at least one liquid charger. As used in this invention, a liquid charger may be any apparatus or combination of apparatuses, which is adapted to be brought in contact with a first side of the sample and which is adapted to apply an extraction liquid to the first side of the sample. The contact between the liquid charger and the sample may be direct or indirect. In any way the contact should be such that the extraction liquid may be applied to the sample, preferably under pressure, preferably by pressing at least part of the extraction liquid into an interior of the sample and preferably through the sample, such as by penetrating one or more surfaces of the sample, e.g. by penetrating one or more surfaces of a leaf of a plant. Alternatively to a direct contact, in which the liquid charger or one or more orifices of the liquid charger, suited for supplying the extraction liquid, directly are in contact with one or more surfaces of the sample, an indirect contact may be provided, preferably a contact, in which the extraction liquid supplied by the liquid charger is guided towards one or more surfaces of the sample, whereby a lateral spreading of the extraction liquid in a direction perpendicular to the application direction may at least partially be avoided. Thus, an indirect contact may be provided by interposing one or more sealing elements in between the liquid charger and the surface of the sample, such as at least one O-ring or other sealing elements. In any case, be it a direct or an indirect contact, the liquid charger should be adapted to provide the extraction liquid to the at least one surface of the sample.

The extraction liquid may be or may comprise any fluid medium, i.e. at least one liquid medium and/or at least one gaseous medium, which may be suited to extract, preferably to selectively extract, the at least one ingredient, which, in the following, may be named the target ingredient. Besides extracting precisely one ingredient from the sample, a combination of ingredients may be extracted, such as a combination of two or more metabolites. Preferably, the extraction liquid comprises at least one solvent, such as an aqueous and/or non-aqueous solvent. Preferably, the solvent may be selected from: aqueous solvents, like water; or non-aqueous solvents, like an organic solvent, preferably one or more of alkylalcohols with an alkyl rest of 1 to 6 carbon atoms, e.g. methanol, ethanol, 1-propanol, 2-propanol, butanol, pentanol, hexanol or aceton, acetonitril, ethylacetate, dimethylsulfoxid or N,N-dimethylformamide, halogenated solvents e.g. chloroform, methylenechloride (dichloromethane), carbontetrachloride, dichloroethane (in particular chloroform, methylenechloride, carbontetrachloride) or aliphatic solvents e.g. hexane, cyclohexane, pentane, heptane etc. or aromatic solvents, e.g. toluene, benzene, or ethers e.g. tert-butylmethylether, diethylether, tetrahydrofurane; or an inorganic solvent, such as an inorganic acid, preferably selected from: HF, HI, HCl, $BF_3$, $BCl_3$, HBr, $HClO_4$, $H_2SO_4$, $H_3PO_4$, especially HI, HCl, HBr, $HClO_4$; or an organic acid such as formic acid, acetic acid, trifluoroacetic acid, trichloro acetic acid; and/or a base, preferably selected from from sodium hydroxide, potassium hydroxide, sodium carbonate, sodium hydrogencarbonate, ammonium acetate, ammonium formiate, ammonium hydrogencarbonate or ammonium carbonate. Further, a combination of the named and/or other solvents may be used.

As mentioned above, the extraction liquid may comprise one or more solvents. In case more than one solvent is used, the solvents may be used simultaneously (such as with constant mixing ratio or with varying mixing ratio, e.g. as gradient) and/or at different times or time-delayed. In case more than one solvent used at the same time, specifically, a mixture of two or more solvents may be used. Thus, in a preferred embodiment, the extraction liquid may comprise a mixture of at least two solvents. Extractions using a mixture of solvents generally is known from EP 1 446 209 B1. Thus, the extraction device may be adapted to provide an extraction liquid containing a mixture of two or more solvents. The extraction device may comprise one or more liquid containers for storing one, two or more solvents to be used as an extraction liquid or to be used as components of the extraction liquid. Further, the extraction device may comprise one or more mixing units for mixing two or more solvents, preferably in a predefined mixing ratio (e.g. especially for batch mode use or for gradient mode use).

Preferably, the at least one mixture may comprise at least one aqueous and at least one non-aqueous solvent. In particular, the mixture may comprise at least one aqueous solvent, like water, and at least one non-aqueous solvent, like an alkyl alcohol. More preferably the mixture comprises methanol and water, preferably in a mixing ratio of 50 Vol-%: 50 Vol-% to 90 Vol-%: 10 Vol-%, and more preferably in a mixing ratio of 80 Vol-%: 20 Vol-%. In another embodiment, the extraction liquid may comprise a mixture of at least two solvents, where the at least two solvents are non-aqueous solvents, in particular the non-aqueous solvents may be selected from the group of alkylalcohols and halogenated solvents. Preferably, the extraction liquid may comprise a mixture of the two solvents methanol and dichloromethane, preferably in a mixing ratio of 20 Vol-%: 80 Vol-% to 60 Vol-%: 40 Vol-% and more preferably in a mixing ratio of 40 Vol-%: 60 Vol-%.

As outlined above, the at least two solvents may be applied to the first side of the biological sample simultaneously and/or in a time-delayed fashion. Thus, in one embodiment of the invention, at least one extraction liquid containing two or more solvents may be applied to the first side of the biological sample to extract at least one ingredient from the sample. Alternatively or additionally, in a further embodiment, the extraction device and/or the method according to the present invention may be adapted to subsequently supply at least two different types of extraction liquids to the first side, such as at least one first extraction liquid and at least one second extraction liquid. Each extraction liquid preferably may comprise one, two or more solvents, such as a mixture of solvents. The liquid supply line may be equipped with at least two different extraction liquids. Preferably, the at least two different extraction liquids are applied subsequently to the first side of the same sample. More preferably, the first extraction liquid may comprise at least two solvents, where one solvent is a non-aqueous solvent and the other solvent is an aqueous solvent and where the second extraction liquid may comprise two non-aqueous solvents. More preferably the first extraction liquid is a monophasic polar solvent mixture and the second extraction liquid is a monophasic apolar solvent mixture. The first extration liquid may comprise methanol and water, preferably in a mixing ratio of 50 Vol-%: 50 Vol-% to 90 Vol-%: 10 Vol-%, and more preferably in a mixing ratio of 80 Vol-%: 20 Vol-%, and the second extraction liquid preferably may comprise methanol and dichlormethane, preferably in a mixing ratio of 20 Vol-%: 80 Vol-% to 60 Vol-%: 40 Vol-% and more preferably in a mixing ratio of 40 Vol-%: 60 Vol-%. Thus, the first extraction liquid may comprise methanol and water in a mixing ratio of 80 Vol-%: 20 Vol-%, and the second extraction liquid may comprise methanol and dichlormethane in a mixing ratio of 40 Vol-%: 60 Vol-%.

In case at least two extraction liquids are used subsequently, such as at least one first extraction liquid and at least one second extraction liquid, the extraction device and/or the method according to the present invention may be adapted to perform at least one first phase of an extraction process, during which the first extraction liquid is applied to the first side of the biological sample, and at least one second phase of the extraction process, during which the second extraction liquid is applied to the first side of the biological sample. These at least two phases may be disjunctive. Thus, the first phase may be performed, wherein, after the first phase is finished, immediately or after performing at least one break or pause during which no extraction liquid is applied to the first side, the second extraction liquid is applied to the first side. However, other embodiments are feasible. Thus, the first phase and the second phase even may overlap during at least one intermediate phase. Thus, the second phase may start when the first phase still is on. During an intermediate phase, both the first extraction liquid and the second extraction liquid may be applied to the first side of the biological sample.

Further, the contents and/or the composition of the at least one extraction liquid applied to the first side of the biological sample may be constant throughout the extraction process. In another embodiment, the contents and/or the composition of the at least one extraction liquid applied to the first side of the biological sample may vary over the extraction process. Therein, stepwise or continuous variations of the composition of the at least one extraction liquid are feasible. Thus, a time variation and/or a time gradient of the content of at least one component of the extraction liquid may be realized. As an example, the content of at least one solvent contained in the extraction liquid may be increased or decreased over a time period, in a stepwise or continuous fashion.

As outlined above, the extraction device and, more specifically, the liquid charger may comprise at least one liquid supply device, such as at least one extraction liquid supply unit, which is adapted to control the composition of the at least one extraction liquid, such as by controlling the content of one or more components of the extraction liquid, such as the content of one or more solvents. Further, the at least one liquid supply device may be adapted to vary the composition of the at least one extraction liquid with time, such as according to a predefined schedule of variation. The liquid supply device preferably may comprise one, two or more valves for adjusting the composition of the extraction liquid, such as valves for connecting a main supply line to two or more supply containers for storing appropriate solvents, thereby allowing to control the composition of the extraction liquid by adjusting the appropriate valves. The valves preferably may be electronically controllable and/or computer-controlled. Preferably, the liquid supply device may comprise a control unit, such as at least one data processing device, e.g. a microcontroller, which may be adapted to control the composition of the extraction liquid according to a predefined schedule or program. The control unit preferably may be adapted to perform at least one software-controlled program for controlling the composition of the extraction liquid.

A liquid supply of the at least one extraction liquid may be part of the extraction device. Thus, the extraction device may comprise one or more orifices, one or more liquid conduits, one or more pumps for supplying the extraction liquid under pressure, a supply, such as one or more reservoirs being capable of storing a supply of the extraction liquid, or an arbitrary combination of the named elements and/or other elements. Besides the possibility of supplying the at least one extraction liquid in one step, such as by supplying one or more extraction liquids simultaneously, several extraction liquids of the same or a different kind may be supplied subsequently, such as by providing a procedure having several steps, wherein in each of the steps a new extraction liquid is supplied.

The extraction device further has at least one sampling device. A sampling device, as used in the present invention, may comprise any apparatus and/or combination of apparatuses, which is adapted to be brought in contact with a second side of the sample and which is adapted to collect sample fluid comprising the at least one extraction liquid and the at least one ingredient. Thus, the extraction device may be adapted to collect at least part of the extraction liquid after passing at least part of the sample and after gathering, such as absorbing and/or solving, the at least one target ingredient. Thus, in the following, the term sample fluid is used for any kind of liquid and/or gaseous fluid, which comprises the at least one extraction liquid and the at least one target ingredient.

Similar to the liquid charger, the sampling device may be adapted to be brought in direct or indirect contact with the second side of the sample. Thus, the sampling device may comprise one or more sampling orifices adapted for collecting the sample fluid, which may be adapted to be brought in direct contact with the second side. Alternatively, one or more elements may be interposed in between the sampling device and the second side, such as at least one sealing element and/or guiding element adapted for guiding the sample liquid to the sampling device. Again, one or more O-rings may be used for preventing sample fluid from leaving the sample without being collected by the sampling device.

The second side, from which the sample fluid is collected, may preferably be different from the first side. Thus, the second side preferably may be a side of the sample opposing the first side. Thus, in case the sample is a leaf or part of a leaf of a plant, the first side may comprise an upper side of the leaf, whereas the second side may comprise a lower side of the leaf or vice versa. Preferably, the first side and the second side are opposing each other in such a way that the extraction liquid may pass the sample from the liquid charger to the sampling device in a straight line. However, other geometries and embodiments are possible.

The liquid charger and the sampling device preferably are connected by at least one connection mechanism. Preferably, this connection mechanism may comprise a mechanical connection. The connection mechanism may be adapted to vary a distance between the liquid charger and the sampling device and to apply a clamping force to the sample located between the liquid charger and the sampling device.

A connection mechanism adapted to vary a distance between the liquid charger and the sampling device may be realized in several ways. Thus, the connection mechanism may comprise at least one actuator, which is adapted for manually or automatically varying the distance. Thus, the connection mechanism may comprise one or more guide elements which are adapted for changing the relative position and/or relative orientation between the liquid charger and the sampling device, such as one or more guide rails, one or more guide bars, one or more linear actuators, one or more stages such as translation stages, one or more pivoting elements or combinations of the named elements and/or other elements.

Preferably, the connection mechanism has at least one hinge, which may be interposed in between the liquid charger and the sampling device. This at least one hinge may be adapted to pivot the liquid charger and the sampling device relative to each other around at least one pivoting axis.

Alternatively or additionally, the connection mechanism may have at least one rail element enabling a relative movement of the liquid charger and the sampling device, preferably a linear relative movement. As used herein, the term relative movement may both refer to a case in which the liquid charger rests and the sampling device is moved and to the case in which the liquid charger is moved and the sampling device rests and to the case in which both the liquid charger and the sampling device are moved.

Further, as used herein, the term rail element may refer to an arbitrary element adapted to guide the relative movement. Most preferably, the rail element may have at least one guiding rod. The at least one guiding rod may fully or partially be part of the liquid charger and/or may fully or partially be part of the sampling device and/or may fully or partially be formed by an independent component or may be part of an independent component of the extraction device. The guiding rod may have a circular or noncircular cross-section and may be or may comprise at least one elongated bar. The sampling device and/or the liquid charger may contain one or more bores or holes, such as one or more blind holes or through holes, which may accommodate the at least one guiding rod or at least one part thereof. Therein, the guiding rod may be fixed inside the at least one hole or bore or may move inside the at least one bore or hole.

In one embodiment, preferably in connection with the above-mentioned rail element, the connection mechanism may be designed such that the liquid charger and/or the sampling device may act as a stamp, exerting a stamping force onto the biological sample. Thus, in one embodiment, the sampling device may act as an anvil, receiving the biological sample, and the liquid charger may act as a stamp stamping the biological sample from the first side, or vice versa. The stamping motion or stamping movement may be supported or guided by the above-mentioned connection mechanism, preferably the rail element and more preferably the one or more guiding rods or other types of guiding rails.

The connection mechanism further may have at least one spring element. As used herein, the term spring element refers to an arbitrary element having at least partially elastic properties, such as an elastic spring, a coil spring, a tongue, an elastomer spring element or a combination of two or more of the named spring elements. The spring element may be adapted to apply a separating force separating the liquid charger and the sampling device. Thus, the at least one spring element may be located in between the liquid charger and the sampling device and may apply at least one separating force to the liquid charger and/or the sampling device, thereby pushing apart or attempting to push apart the liquid charger and the sampling device, in order to open a space in between the liquid charger and the sampling device for insertion of the biological sample. Thus, the at least one spring element may comprise at least one coil spring which fully or partially surrounds the above-mentioned at least one optional rail element, such as the at least one guiding rod.

The variation of the distance between the liquid charger and the sampling device may comprise any change in a relative position of the liquid charger and the sampling device, in one or more dimensions. Thus, a variation of the distance may comprise a change in a one-dimensional or multi-dimensional distance between the named elements and/or may comprise a rotation of the liquid charger and the sampling device relative to each other around at least one rotational axis. Alternatively or additionally, the variation of the distance may comprise a linear relative movement of the liquid charger and the sampling device, wherein both the liquid charger and the sampling device may move or wherein either the liquid charger or the sampling device may move.

A clamping force may comprise any force which is applied to the sample by the liquid charger and/or the sampling device, once the sample is clamped in between these elements. Preferably, the connection mechanism is adapted to allow for homogeneously applying pressure to the sample, independently from the sample thickness. The term homogeneously may comprise any situation, in which the clamping force and/or pressure applied by the extraction device to the sample is the same or at least similar in any area in which the clamping force is applied. Variations of the pressure of up to 20%, preferably of no more than 10% and most preferably of no more than 5% may be acceptable and may still be summarized under the term homogeneous, as used in the present invention. The named embodiment of the independence of the applied pressure from the sample thickness may be achieved in several ways. Firstly, this independence may apply within a certain acceptance range of sample thicknesses, such as an acceptance range of 0 to 30 mm (i.e. more than 0 mm and less or equal 30 mm) thickness of the sample, preferably 0 to 20 mm (i.e. more than 0 mm and less or equal 20 mm) of sample thickness, preferably 0 to 10 mm (i.e. more than 0 mm and less or equal 10 mm) of sample thickness and most preferably 0 to 5 mm (i.e. more than 0 mm and less or equal 5 mm) of sample thickness. The homogeneous application of pressure, independent from the sample thickness, may e.g. be achieved by providing appropriate guiding elements for adapting the distance between the liquid charger and the sampling device, such as one or more of the guide elements listed above. Thus, one or more linear stages for varying the distance may be provided, and/or the sampling device and the liquid charger may be connected to each other in a way the chops or jaws of a pipe tong are connected to each other, allowing for a simultaneous adaption of a linear distance and an angle between the liquid charger and the sampling element. Other connection mechanisms, which are adapted for providing a homogeneous application of pressure may be possible.

Generally, the sampling area, which is the area of the sample to which the extraction liquid may be applied by using the extraction device, such as an area of the biological sample perpendicular to direction of supply of the extraction liquid, may vary over a wide range. Thus, the sampling area may be in the range of $1\ mm^2$ to $50\ cm^2$, preferably $5\ mm^2$ to $10\ cm^2$. However, other sampling areas may be realized.

As outlined above, the liquid charger and the sampling device may be connected in several ways. Most preferably, the extraction device comprises one or more grippers. Thus, the liquid charger and the sampling device, taken alone or in combination with one or more other elements, may form a gripper or pincer for gripping the sample. A gripper or pincer, as used in the present invention, may comprise any element which is adapted for gripping the sample and applying a clamping force to the sample, in between the liquid charger and the sampling device. Thus, a gripper or pincer may comprise one or more of the following forms: a gripper, a pincer, a tong, a plier, a forceps, a caliper, a pipe tong, a clamp, preferably a screw clamp and/or a bar clamp; a tweezer. Other embodiments are possible. The at least one gripper may be integrated into the liquid charger and/or the sampling device and may be a part of one or both of these elements or one or both of the elements may be part of the at least one gripper. Alternatively or additionally, the at least one gripper may be a separate element which may act on the liquid charger and/or the sampling device.

Thus, the gripper may exert a clamping force adapted to press the liquid charger against the sampling device or vice versa and/or to press the liquid charger and/or the sampling device against the biological sample.

The extraction device may preferably be a hand-held device. Within the present invention, the term hand-held device may comprise any device which is adapted to be held and/or carried by a single person, preferably by one hand. In case the extraction device comprises further elements besides the liquid charger and the sampling device, at least the part comprising the liquid charger and the sampling device, preferably the gripper or pincer, should be designed to be a hand-held device. Other parts of the extraction device, such as a liquid supply, a pump or other parts may, alternatively or additionally to being at least partially integrated into the hand-held device, designed to be stationary components, such as stationary laboratory components. The hand-held device may have a volume which preferably does not exceed $5 \times 10^6$ mm$^3$ and preferably does not exceed $1 \times 10^6$ mm$^3$, most preferably $0.5 \times 10^6$ mm$^3$.

As outlined above, the first and second sides of the sample, i.e. the side to which the extraction liquid is applied and the side from which the sample fluid is collected, each may comprise one or more positions on a surface of the sample. Preferably, the first and second sides are opposing sides of the sample. This means that the extraction liquid may pass from the liquid charger to the sampling device preferably in a straight line. This straight line may preferably be essentially perpendicular to the surface of the sample on the first side and/or the second side, which comprises deviations from a perpendicular orientation by preferably no more than 20°, preferably no more than 10°. The surface of the sample may be a simple, flat surface. Alternatively or additionally, the surface of the sample may comprise a rough or even undefined surface, such as in mashed or milled samples. Most preferably, the sample is an intact part of a plant in good order, such as a leaf and/or a part of a leaf of a plant.

As outlined above, the liquid charger and the extraction device may be brought in direct or indirect contact with the first side or the second side, respectively. Thus, the liquid charger may comprise at least one first sealing element, which is adapted to be pressed against the first side of the sample. The sealing element may comprise any element adapted for guiding the extraction liquid from the liquid charger, such as from at least one orifice of the liquid charger adapted for supplying the extraction liquid, to the first side. Preferably, the at least one first sealing element may comprise at least one O-ring.

The liquid charger may comprise at least one liquid supply line and at least one orifice. The liquid supply line may be adapted to provide the at least one extraction liquid to the at least one orifice. The liquid supply line may itself comprise a reservoir being capable of holding a supply of the at least one extraction liquid. Alternatively or additionally, the supply line may be adapted to be directly or indirectly connected to at least one liquid supply for supplying the extraction liquid. The at least one orifice may comprise any type of opening in at least one surface of the liquid charger, which preferably may face the first side of the sample. This at least one opening may have an arbitrary geometric shape, such as the shape of a simple hole, a nozzle, a line of holes, a grid of holes, an array of holes or any other shape. Thus, the at least one orifice may comprise at least one perforated plate having one or more perforations through which the extraction liquid may pass. The at least one orifice may preferably be fully surrounded by the at least one optional first sealing element, such as by the at least one O-ring. The at least one sealing element preferably may be at least partially be flexible and/or deformable. Thus, the at least one first sealing element may comprise an elastomeric material, such as a rubber. This flexible and/or deformable property may help to adapt the shape of the surface of the sample to the shape of the liquid charger.

The extraction device, as outlined above, may further comprise at least one second sealing element, which is adapted to be pressed against the second side of the sample, specifically at least one O-ring. The at least one second sealing element may be embodied in the same way as the at least one first sealing element. Thus, the above-mentioned optional properties of the first sealing element may apply to the at least one second sealing element.

The extraction device preferably has at least one sample opening adapted to collect the sample fluid. This collection of sample fluid may comprise any acceptance of the sample fluid, which may be in a directional or non-directional way. Similar to the at least one orifice of the liquid charger, the sample opening may have an arbitrary shape and/or geometry. Preferably, the at least one sample opening may have a larger diameter or equivalent diameter than the orifice of the liquid charger. Similar to the orifice, the opening may have any geometric shape, such as a round shape, a polygonal shape or any other shape. The at least one opening may comprise a single opening or a plurality of openings, such as a line and/or grid and/or array of openings. This applies to an embodiment, in which a second sealing element is used as well as to embodiments, in which no second sealing element is present. The at least one opening may comprise an opening having a constant diameter or, preferably, may comprise an opening having a varying shape in a direction of a flow of the sample fluid, such as a shape of a cone and/or a funnel, for supporting the collection of the sample fluid from the second side.

The liquid charger may preferably have a ring-shaped first sealing element, adapted to be pressed to the first side of the sample. The sampling device may have a ring-shaped second sealing element adapted to be pressed against the second side of the sample. The first and the second sealing elements may each be connected and/or being part of the liquid charger or the sampling device, respectively, or may be separate elements, which may be handled independently from the liquid charger and/or the sampling device. The first and second sealing elements may preferably be arranged such that they are adapted to be pressed against each other on opposing sides of the sample, with the sample in between, thereby creating an extraction region within the sample. However, other embodiments are possible.

The sampling device preferably may have at least one sampling vessel, and the sampling device may be adapted to at least partially guide the sample fluid into the sampling vessel. This sampling vessel may comprise one or more sampling vessels and may be a permanent part of the sample device or may be adapted to be replaceable. Preferably, the sampling vessel is arranged in the sample device in a replaceable way. Thus, the extraction device and preferably the sampling device may comprise one or more connection elements and/or receptacles, which may be adapted to connect to the at least one sampling vessel, preferably by a form-fit and/or a force-fit connection, preferably in a reversible way.

For at least partially guiding the sample fluid into the sampling vessel, the sampling device may comprise one or more guides, such as a sample fluid line leading the sample fluid directly and/or indirectly into the sampling vessel. Thus, the sampling vessel may be connected to the at least one optional sample opening. As outlined above, preferably, the at least one guide element may comprise at least one funnel.

The sampling vessel preferably has at least one inert material. These inert properties preferably refer to the sample fluid, and most preferably to the extraction liquid, such as to at least one solvent comprised in the extraction liquid. Thus, preferably, the inert material is chosen such that the sample fluid and preferably the extraction liquid does not change the chemical composition of the inert material and/or extracts one or more components from the inert material. Most preferably, the at least one inert material is chosen from a glass, a quartz, a ceramics material, a fluorinated plastic material, specifically PTFE. However, a combination of the named materials and/or other materials is possible, as well as the choice of a different material.

The sampling device further may comprise at least one pressure adjusting element which is adapted to adjust a gas pressure inside the sampling vessel. Thus, the at least one pressure adjusting element may be adapted to adjust the gas pressure inside the sampling vessel to a specific, pre-defined pressure, such as an ambient pressure. Thus, a pressure balance may be achieved, preferably a pressure balance between the inside of the sampling vessel and the surrounding atmosphere. Preferably, the at least one pressure adjusting element may comprise at least one valve and/or release opening.

The sampling device may further have at least one gas inlet, which is adapted to expose at least one interior space of the sampling vessel with gas, specifically with an inert gas. Thus, the sampling vessel may partially or fully be flooded with one or more pre-defined gases, preferably for protecting the sample fluid from unwanted reactions, such as oxidation. Thus, the at least one inert gas may comprise inert gases such as nitrogen and/or argon. The at least one gas inlet may at least partially be part of the sampling device, such as by providing at least one orifice and/or nozzle in one or more of the walls of the sampling device. Additionally or alternatively, the at least one gas inlet of the sampling device may comprise a gas inlet, which is part of other parts of the extraction device, such as of the sampling device, such as by providing an end of a gas tube, which extends into an interior space of the sampling vessel. The gas inlet may be connected to one or more gas lines, for providing the gas, such as to a supply line being part of a building and/or to a gas cylinder. Further elements may be provided, such as pressure-reducing valves and/or other elements.

The sampling device may further be adapted to prevent ambient light from entering the sampling vessel. This may be achieved by corresponding properties of the sampling vessel and/or other parts of the sampling device. Thus, the sampling vessel may at least partially be made of an intransparent or opaque material, which filters at least part of the ambient light, such as ultraviolet light. Additionally or alternatively, the sampling vessel may be accommodated in a receptacle inside the sampling device, thereby being protected at least partially from the ambient light, and/or may be shielded by the sampling device from the ambient light in any other way, such as by using at least one shielding element. This protection from ambient light may further prevent unwanted reactions inside the sample fluid, such as photooxidations or photochemical reactions.

The sampling vessel may preferably be a lockable vessel, such as a bottle and/or vial, being lockable by at least one locking element. Preferably, the at least one locking element may comprise a lid and/or a cap. Thus, the at least one sampling vessel may comprise a screw-cap bottle and/or a snap-on-lid bottle. Other types of sampling vessels are possible.

The sampling device preferably has at least one sample tempering element, wherein the sample tempering is adapted to temper, specifically to cool, the sample fluid. As used herein, a tempering element may comprise any apparatus or combination of apparatuses adapted for controlling, preferably regulating, a temperature of the sample fluid, preferably to at least one predetermined temperature, which may be fixed or which may have predetermined temporal characteristics. The at least one predetermined temperature may be below ambient temperature, above ambient temperature or may be ambient temperature. Preferably, as outlined above, the sample tempering element is adapted for cooling the sample fluid. Cooling of the sample fluid may further prevent the sample fluid from unwanted chemical reactions. The cooling may be adapted such that the sample fluid still is in a gaseous and/or liquid state. Alternatively, the cooling may be such that the sample fluid is frozen.

As outlined above, the sampling device may comprise one or more guide elements, which may be adapted to guide the sample fluid leaving the sample. Preferably, the sampling device has at least one funnel for receiving the sample fluid. This funnel may be adapted to collect sample fluid from a larger area on the second side and guide sample fluid from this larger area into a smaller liquid channel and/or sampling vessel.

The extraction device may further have at least one filter element for filtering the sample fluid. This filter element may be adapted for retaining one or more components of the sample fluid, such as solid components. Thus, components of the skeleton of the sample may be retained, such as solid parts of a leaf, trunk, stem, root, storage root, branch, inflorescence, flower, infructescence, fruit, ear, cob, seed or any other part of a plant, whereas liquid components contained in the sample fluid may be allowed to pass. Preferably, the at least one filter element may comprise at least one frit or ceramic filter element. However, other filter elements are possible. The filter element may be located on or inside the extraction device in an arbitrary way. Thus, the filter element may be part of or be connected with the at least one optional sample opening, with the at least one optional funnel, with at least one channel leading from the at least one sample opening to the at least one sampling vessel and/or with the at least one sampling vessel. Preferably, the at least one filter element may be selected from the group consisting of: a mesh; a screen; a sieve; a grill; a perforated plate having one or more perforations.

Further, the extraction device may have at least one absorbing material adapted for absorbing the ingredient(s) and preferably for enrichment and/or depletion of the ingredient(s). This absorbing material preferably may be adapted to absorb one or more ingredients from the sample fluid, such as by locating the absorbing material in a fluid path of the sample fluid and/or in a sampling vessel adapted to collect the sampling fluid or parts thereof.

As outlined above, the liquid charger may have at least one pressurizing element. This pressurizing element may be adapted to provide the extraction liquid in a pressurized way, i.e. under a pressure which is above normal pressure. Thus, the pressure of the extraction liquid may preferably be in the range of 1 bar to 20 bar, preferably in the range of 2 bar to 8 bar. The pressurizing element may be integrated into the extraction device and preferably into the liquid charger. Alternatively or additionally, the at least one pressurizing element may comprise one or more external elements, such as an external pressure source. Preferably, the pressurizing element may comprise one or more pumps and/or pressurized supply elements for supplying the extraction liquid under pressure.

The extraction device and most preferably the liquid charger may further comprise one or more valves, preferably one or more valves adapted to control a pressure and/or a flow of the extraction liquid. Thus, at least one valve may be provided in a supply line for supplying the extraction liquid. The at least one valve may be adapted to switch on or switch off a flow of the extraction liquid. Alternatively or additionally, the at least one valve may be adapted to adjust a flow and/or a pressure of the extraction liquid in a stepless way or in two or more steps. Again, alternatively or additionally, the at least one valve may prevent a backflow of the extraction liquid from the liquid charger back into the supply line. Thus, preferably, the at least one valve may comprise at least one back-pressure valve.

The extraction device and preferably the liquid charger may further have at least one extraction liquid tempering element, which is adapted to temper the extraction liquid. With regard to the term tempering, the same as outlined above with regard to tempering the sample fluid applies. Thus, the tempering may be above, below or at room temperature. Thus, the tempering element may comprise a heating element and/or a cooling element. As is the case for the sample tempering element, the extraction liquid tempering element may thus comprise one or more heating and/or cooling pipes and/or coils, one or more resistive heaters, one or more peltier elements and/or other tempering elements. Thus, the extraction liquid tempering element may be adapted to control a temperature of the extraction liquid to at least one predetermined temperature or temperature range.

The sampling device, preferably the sampling vessel and/or another part of the sampling device, such as an optional filter element, may further be adapted to at least partially condition the sample fluid. Thus, the sampling device may have at least one absorbing material adapted for absorbing the ingredient(s) and preferably for enrichment and/or depletion of the ingredient(s). However, other types of sample conditioning and/or sample enrichment and/or sample depletion are possible. The absorbing material may e.g. be part of the sampling vessel and/or the filter element and/or maybe located in any other location of the sampling device, such as in a location in between the filter element and the sampling vessel, such as in a location under the filter element.

The conditioning of the sample fluid may preferably comprise an enrichment and/or depletion by using one or more absorbing materials which are passed by the sample fluid. Thus, the sampling device may be adapted such that the sample fluid is pressed through the absorbing material located in the filter element and/or the sampling vessel or located in any other way. Similar to a solid phase extraction (SPE), one or more types of molecules may stick to the absorbing material, such as lipids. Other types of molecules may pass the absorbing material and may reach the sampling vessel. Thus, by using one or more absorbing materials, the sampling device may be adapted to separate two or more fractions of the sample fluid. One or more of these fractions may be of interest for further use. Thus, the fraction of the sample fluid passing the absorbing material and reaching the sampling vessel may be used and/or the fraction of the sample fluid absorbed by the absorbing material may be used, such as for further analysis. Thus, the absorbing material comprising the absorbed fraction may be treated with one or more solvents, in order to separate the fraction from the absorbing material for further use, such as for analyzing lipids up sold by the absorbing material.

One or more chemical materials may be comprised in the sampling device, such as in the sampling vessel and/or in the absorbing material and/or in the filter element and/or in any other location of the sampling device almost such as between the filter element and the sampling vessel, e.g. for performing one or more analytical reactions and/or for sample conditioning. Thus, one or more buffer chemicals may be comprised. Thus, the sampling device and preferably the sampling vessel may have at least one reagent adapted to react with the sample fluid and/or the ingredient, preferably for stabilizing the ingredient.

In a further aspect of the present invention, a method for extracting at least one ingredient from a biological sample is disclosed. The method may preferably be performed by using the extraction device according to one or more of the embodiments disclosed above. Consequently, with regard to preferred embodiments of the method, reference may be made to the extraction device mentioned above. However, the use of other types of extraction devices and/or other devices is possible.

The method may preferably be used for extracting one or more metabolites from a plant specimen. However, other uses of the method according to the present invention, i.e, the extraction of other types of target ingredients, are possible, as well as the use of samples other than plant specimens, such as other types of biological samples (e.g. sea weed).

The method comprises the step of bringing at least one liquid charger in contact with a first side of the sample. At least one extraction liquid, specifically at least one solvent, is applied to the first side of the sample by using the liquid charger. In a further method step, at least one sampling device is used, which is brought in contact with a second side of the sample. Sample fluid comprising the extraction liquid and the ingredient is collected by using the sampling device. The sample may preferably be clamped between the liquid charger and the sampling device.

In a further aspect of the present invention, a method for extracting at least one metabolite from a biological sample, specifically from a plant specimen, is disclosed. In this method, an extraction device according to one or more of the embodiments disclosed above, is used. Thus, with regard to preferred embodiments of this method, reference may be made to the extraction device as disclosed above.

Summarizing, the following items are specifically preferred within the present invention:

Item 1: An extraction device for extracting at least one ingredient from a biological sample, specifically for extracting metabolites from a plant specimen, the extraction device having at least one liquid charger, wherein the liquid charger is adapted to be brought in contact with a first side of the sample and wherein the liquid charger is adapted to apply an extraction liquid, specifically at least one solvent, to the first side of the sample, the extraction device further having at least one sampling device, wherein the sampling device is adapted to be brought in contact with a second side of the sample and wherein the sampling device is adapted to collect sample fluid comprising the extraction liquid and the ingredient.

Item 2: The extraction device according to the preceding item, wherein the liquid charger and the sampling device are connected by at least one connection mechanism, wherein the connection mechanism is adapted to vary a distance between the liquid charger and the sampling device and to apply a clamping force to the sample located between the liquid charger and the sampling device.

Item 3: The extraction device according to the preceding item, wherein the connection mechanism has at least one hinge.

Item 4: The extraction device according to one of the two preceding items, wherein the connection mechanism has at least one rail element enabling a relative movement of the liquid charger and the sampling device, preferably a linear relative movement.

Item 5: The extraction device according to the preceding item, wherein the rail element has at least one guiding rod.

Item 6: The extraction device according to one of the four preceding items, wherein the connection mechanism has at least one spring element, wherein the spring element is adapted to apply a separating force separating the liquid charger and the sampling device.

Item 7: The extraction device according to one of the preceding items, wherein the extraction device is a hand-held device.

Item 8: The extraction device according to one of the preceding items, wherein the liquid charger has at least one first sealing element which is adapted to be pressed against the first side of the sample, specifically at least one O-ring.

Item 9: The extraction device according to one of the preceding items, wherein the extraction device has at least one second sealing element which is adapted to be pressed against the second side of the sample, specifically at least one O-ring.

Item 10: The extraction device according to one of the preceding items, wherein the sampling device has at least one sampling vessel, wherein the sampling device is adapted to at least partially guide the sample fluid into the sampling vessel.

Item 11: The extraction device according to the preceding item, wherein the sampling vessel is arranged in the sampling device in a replaceable way.

Item 12: The extraction device according to one of the two preceding items, wherein the sampling device has at least one pressure adjusting element adapted to adjust a gas pressure inside the sampling vessel.

Item 13: The extraction device according to one of the three preceding items, wherein the sampling device has at least one gas inlet adapted to expose at least one interior space of the sampling vessel with gas, specifically with an inert gas.

Item 14: The extraction device according to one of the preceding items, wherein the sampling device has at least one sample tempering element, wherein the sample tempering element is adapted to temper the sample fluid.

Item 15: The extraction device according to one of the preceding items, wherein the sampling device has at least one funnel for receiving the sample fluid.

Item 16: The extraction device according to one of the preceding items, wherein the extraction device has at least one filter element for filtering the sample fluid.

Item 17: The extraction device according to the preceding item, wherein the filter element is selected from the group consisting of: a mesh; a screen; a sieve; a grill; a perforated plate having one or more perforations.

Item 18: The extraction device according to one of the preceding items, wherein the liquid charger has at least one pressurizing element, wherein the pressurizing element is adapted to provide the extraction liquid in a pressurized way.

Item 19: The extraction device according to one of the preceding items, wherein the extraction device, preferably the liquid charger, has at least one valve, preferably a back-pressure valve.

Item 20: The extraction device according to one of the preceding items, wherein the liquid charger has at least one extraction liquid tempering element, wherein the extraction liquid tempering element is adapted to temper the extraction liquid.

Item 21: The extraction device according to one of the preceding items, wherein the sampling device has at least one absorbing material adapted for absorbing the ingredient and preferably for enrichment and/or depletion of the ingredient.

Item 22: An extraction system, comprising at least one extraction device according to one of the preceding items, the extraction system further comprising at least one biological sample, preferably at least one plant specimen, wherein the biological sample is clamped between the liquid charger and the sampling device.

Item 23: The extraction system according to the preceding item, wherein the biological sample comprises a sample taken from a living being or entity, preferably as an intact part, preferably a plant or plant part.

Item 24: The extraction system according to one of the two preceding items, wherein the biological sample comprises living cells.

Item 25: A method for extracting at least one ingredient from a biological sample, specifically for extracting at least one metabolite from a plant specimen, preferably by using the extraction device according to one of the preceding items, wherein a liquid charger is brought in contact with a first side of the sample and wherein an extraction liquid, specifically at least one solvent, is applied to the first side of the sample by using the liquid charger, wherein further at least one sampling device is used, wherein the sampling device is brought in contact with a second side of the sample and wherein a sample fluid comprising the extraction liquid and the ingredient is collected by using the sampling device.

The extraction device and the methods according to the present invention provide a large number of advantages over known devices and methods. Preferably, the extraction device may be used directly on plants grown in a field, a greenhouse or a growth chamber. Thus, the extraction of the at least one ingredient from the biological sample may take place without or with significantly reduced effort regarding the sample preparation. Thus, the extraction may even take place without separating the sample from the remaining biological entity, such as without removing the leaf, trunk, stem, root, storage root, branch, inflorescence, flower, infructescence, fruit, ear, cob or seed from the remaining plant. Specifically, the extraction device may simply be clamped onto the leaf, trunk, stem, root, storage root, branch, inflorescence, flower, infructescence, fruit, ear, cob or seed, and the extraction may take place, without cutting the plant into pieces. Thus, besides significantly reducing the effort for sample preparation and, thus, reducing the time consumption for sample preparation, the stress exerted onto the sample, such as onto the plant, by sample preparation may be significantly reduced. This may help to prevent the sample from unwanted reactions induced by stress.

Further, when testing a large number of samples, such as typically performed when testing new active agents, the tact time or turnaround time for each extraction may be reduced significantly. Thus, a mass-screening of a large number of active agents or components may be possible, by applying these active agents to a biological entity, such as a plant, and by rapidly extracting one or more metabolites from this entity, for further investigation and/or analysis. Consequently, a database comprising a large number of metabolite profiles of treatments of various kinds may be composed by using the methods and devices according to the present invention.

DESCRIPTION OF THE DRAWINGS

For a more complete understanding of the present invention, reference is established to the following description of preferred embodiments, made in connection with accompanying drawings. The invention, however, is not restricted to these embodiments. Identical reference numbers in the drawings refer to identical and/or functionally equivalent elements in the embodiments.

In the drawings.

PREFERRED EMBODIMENTS

Figure 1:
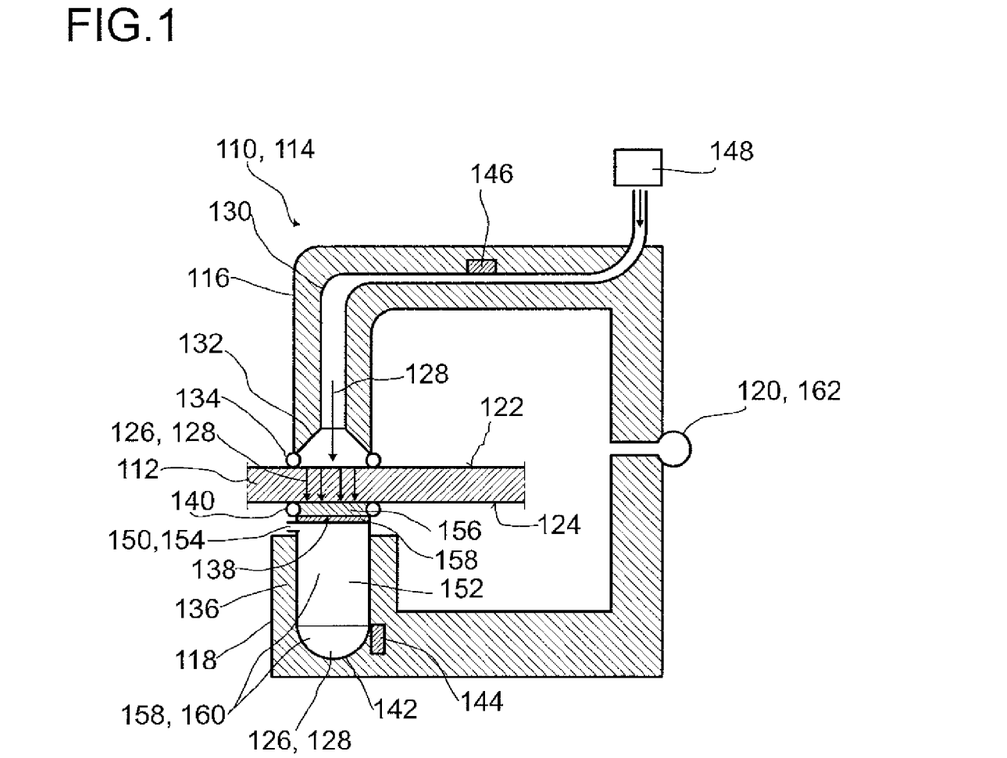
FIG. 1 shows a first embodiment of an extraction device according to the present invention in a cross-sectional view.

In FIG. 1, a cross-sectional view of a first embodiment of a preferred extraction device 110 according to the present invention is shown. The extraction device 110 is used for extracting at least one ingredient from a biological sample 112, such as a leaf of a plant or another sample. In this embodiment and in the following, the extraction device 110 and the biological sample 112 in combination may form an extraction system or parts of an extraction system, which is not separately denoted by a reference number in the figures. Further, herein, the terms biological sample and sample are used as synonyms. However, it has to be understood that other types of samples may be used.

The extraction device 110 in the present embodiment is designed like a tong 114, comprising a liquid charger 116 and a sampling device 118 as chops of the tong, which are connected by a hinge 120, thereby allowing for clamping the sample 112 in between the liquid charger 116 and the sampling device 118. The liquid charger 116 is adapted to be brought in contact with a first side 122 of the sample 112, whereas, in the present embodiment, the sampling device 118 is adapted to be brought in contact with a second side 124, which opposes the first side 122, thereby allowing for a sample fluid 126 and/or an extraction liquid 128 to pass through the sample 112, preferably in a straight line.

The liquid charger 116 comprises a liquid supply line 130 adapted for providing an extraction liquid to the first side 122 of the sample. The liquid supply line 130 leads to at least one orifice 132 facing the sample 112, which, as depicted in FIG. 1, may optionally comprise a widening, such as a funnel, facing the sample 112. In between the orifice 132 and the first side 122 of the sample 112, a first sealing element 134, such as an O-ring, may be provided. Preferably, this first sealing element 134 provides a sealing effect all around the orifice 132. The liquid supply line 130 may be connected to an extraction liquid reservoir, and the extraction liquid may be provided under pressure.

On the second side 124, the sampling device 118 comprises at least one sampling vessel 136, having an opening 138 facing the second side 124 of the sample 112. In between this opening 138 and the second side 124 of the sample 112, a second sealing element 140 may be provided, which, again, may provide a sealing effect all around the opening 138. Again, one or more O-Ring may be used, such as one or more O-rings located on top of a rim of the sampling vessel 136 facing the second side 124 of the sample 112.

The sampling vessel 136 is adapted for receiving the extraction liquid 128 and/or the sample fluid 126 collected from the second side 124 of the sample 112. The sampling vessel 136 may be made of any suitable material or combinations of materials. Preferably, the sampling vessel 136 is made of an inert material, such as glass and/or Teflon. However, other types of materials are possible. The receptacle 142 may comprise at least one sample tempering element 144, which is symbolically depicted in FIG. 1 and which may be adapted to temper the extraction liquid 128 and/or the sample fluid 126 collected inside a sampling vessel 136. Similarly, the extraction liquid 128 may be provided in a tempered way, such as by using an extraction liquid tempering element 146, which is symbolically depicted in FIG. 1. However, other types of tempering elements 144, 146 are possible, as well as other locations of these tempering elements 144, 146 than the positions depicted in FIG. 1. Further, the extraction device 110 may comprise at least one pressurizing element 148, which is symbolically depicted in FIG. 1, which may be adapted to provide the extraction liquid 128 in a pressurized way.

The sampling vessel 136 may further comprise at least one pressure adjusting element adapted for adjusting a gas pressure inside an interior space 152 of the sampling vessel 136. Alternatively or additionally, the sampling vessel may comprise at least one gas inlet 154 for applying at least one gas into the interior space 152 of the sampling vessel 136, which may be separate from the pressure adjusting element 150 or, as in FIG. 1, which may at least partially be identical to the pressure adjusting element 150. Via this gas inlet 154, an inert gas or protective gas may be supplied to the interior space 152, in order to prevent unwanted reactions.

The extraction device 110 and preferably the sampling device 118 and/or any other location of the extraction device 110 may further comprise one or more filter elements 156. In the preferred embodiment depicted in FIG. 1, this filter element 156 may e.g. comprise one or more frits, such as a frit located inside an O-ring of the second sealing element 140.

Further, the extraction device 110 may further comprise one or more absorbing materials 158 and/or reagents 160, as symbolically depicted in FIG. 1. Thus, absorbing materials 158 may be used, which are adapted for enrichment and/or depletion of one or more specific metabolites. The absorbing materials 158 and/or reagents 160 may be located in several ways, such as being part of the filter element 156 and/or being part of the sampling vessel 136 and/or being comprised in the sampling vessel 136 and/or being located in between the filter element 156 and the sampling vessel 136. However, other embodiments are possible.

For using the extraction device 110 according to FIG. 1, the sample 112, such as a leaf, e.g. a leaf of a corn plant, may be clamped in between the liquid charger 116 and the sampling device 118. Thus, the liquid charger 116 may be applied to the first side 122, and the sampling device 118 may be supplied to the second side 124 or vice versa. Extraction liquid 128 is supplied via the liquid supply line 130 to the orifice 134, preferably under pressure. The extraction liquid 128 may preferably comprise one or more solvents, preferably at a specific, pre-determined temperature. This temperature may be controllable to a pre-determined temperature from the cold temperature range to a hot temperature range. The extraction liquid 128 may be pressed through the sample 112 by applying a sufficient pressure, such as in a typical vaccination procedure by using a vaccination pistol. The sample fluid 126, comprising the extraction liquid 128 and one or more target ingredients, is collected inside the sampling vessel 136.

Via the pressure adjusting element 150, a pressure adjustment in the interior space 152 of the sampling vessel 136 may be provided. This pressure adjustment may be performed with pre-defined standards, such as internal standards and/or external standards, qualitatively as well as quantitatively. The pressure adjusting element 150 preferably may comprise an active valve and/or a passive valve and/or a capillary, such as a restriction capillary.

The sampling vessel 136 may preferably be coolable and protected from ingression of light and/or other radiation, in order to prevent oxidation reactions. Further, the sampling vessel 136 may be tightly closable before and after the extraction, such as by using a screw cap and/or a snap-on cap vessel. Further, during the extraction procedure itself, the first and second sealing elements 134, 140 may provide a tight sealing against the sample 112, which may simultaneously provide a sealing of the sampling vessel 136.

The hinge 120 or any other connection mechanism 162 adapted for connecting the liquid charger 116 and the sampling device 118 may preferably be designed such that the pressure onto the first and second sealing elements 134, 140 is homogeneous and equal, independent from the thickness of the sample 112, such as the thickness of a leaf.

The filter element 156 may preferably be adapted to prevent remainders of tissue of the sample 112 to enter the sampling vessel 136. Inside the sampling vessel 136, one or more further reagents 160 may be provided, preferably reagents 160 adapted for stabilizing the sample fluid 126, preferably one or more of the ingredients extracted from the sample 112. Thus, Butylhydroxy toluene (BHT) and/or diatomaceous earth and/or other reagents 160 may be comprised in the sampling vessel 136.

Figure 2:
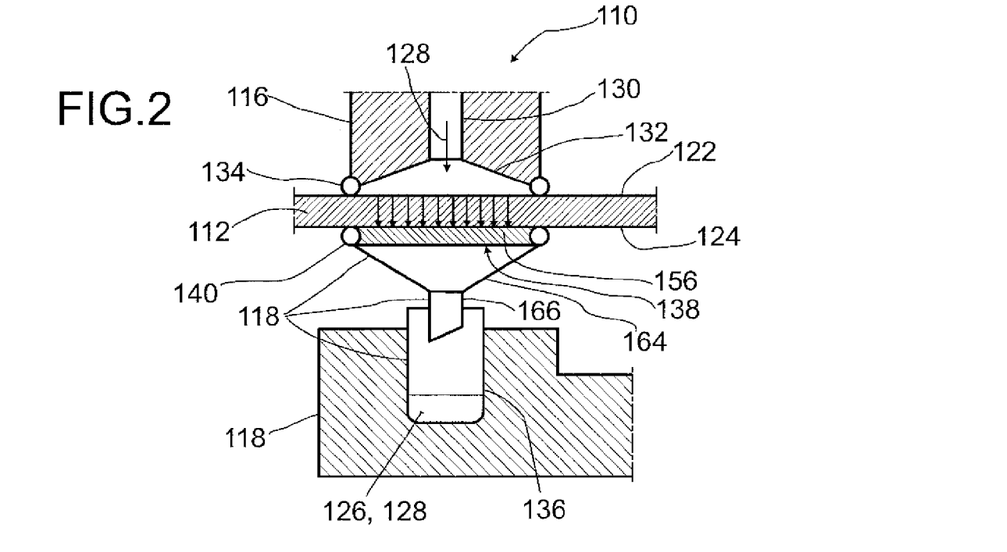
FIG. 2 shows a partial view of a second embodiment of an extraction device according to the present invention.

In FIG. 2, a second embodiment of an extraction device 110 according to the present invention is depicted in a similar view as shown in FIG. 1. Only an extraction region in between the liquid charger 116 and the sampling device 118 is shown. For other components of the extraction device 110, reference may be made to the above-mentioned embodiment.

The extraction device 110 in FIG. 2 comprises a liquid charger 116, which may be designed in a similar way as in the above-mentioned embodiment according to FIG. 1. Thus, reference is made to the above-mentioned description. Contrarily to the embodiment of FIG. 1, however, the sampling device 118 in this embodiment comprises a funnel 164 for collecting sample fluid 126 from larger areas of the second side 124 of the sample 112. This funnel 164 may be separate from the sample vessel 136 or may be part of the sampling vessel 136 or other parts of the sampling device 118, which may comprise further parts than the parts depicted in FIG. 2. On its upper end, the funnel 164 may, again, comprise at least one second sealing element 140 as well as at least one filter element 156, similar to the embodiment shown in FIG. 1. The funnel 164 may comprise one or more adapters and/or ports 166 adapted for guiding the sample fluid 126 into the sampling vessel 136. Further preferred embodiments of a device shown in FIG. 1 may be applied to the embodiment shown in FIG. 2, such as the sample tempering element 144, the extraction liquid tempering element 146, the pressurizing element 148, the pressure adjusting element 150, the gas inlet 154, the absorbing material 158 or the reagent 160. Reference may be made to the embodiment of FIG. 1 as described above.

Figure 3:
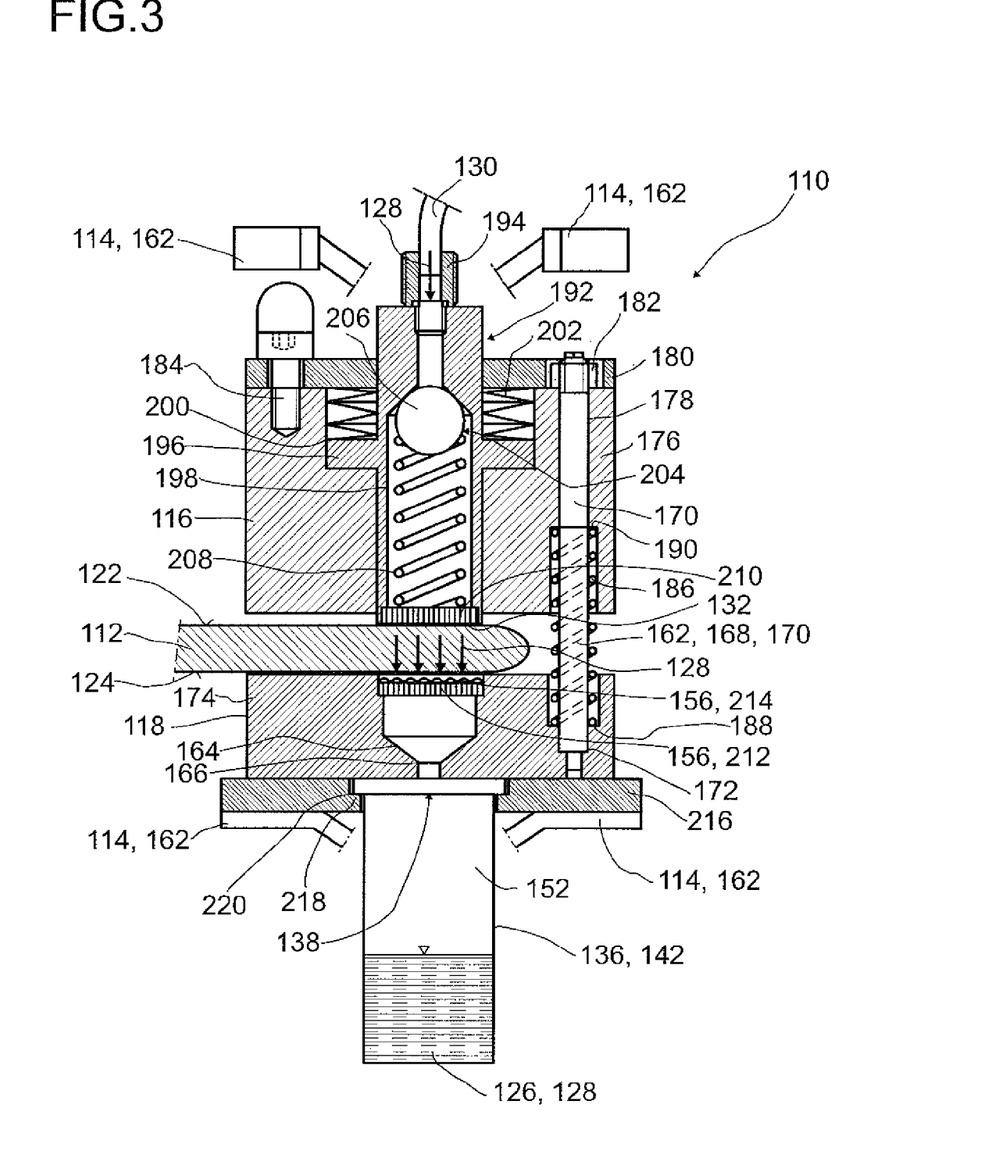
FIG. 3 shows a cross-sectional view of a third embodiment of an extraction device according to the present invention.

In FIG. 3, a cross-sectional view of a third embodiment of an extraction device 110 according to the present invention is depicted. To a large extent, reference may be made to the above-mentioned embodiments.

Again, the extraction device 110 comprises a liquid charger 116 adapted to be brought in contact with a first side of a biological sample 112 and adapted to apply an extraction liquid to the first side 122. Further, the extraction device in this third embodiment again comprises a sampling device 118 adapted to be brought into contact with a second side 124 of the biological sample 112 and adapted to collect sample fluid 126 leaving the biological sample 112.

Again, the liquid charger 116 and the sampling device 118 are connected by a connection mechanism 162 which is adapted to vary a distance element 116 and 118 and which is adapted to apply a clamping force to the sample 112 located between the liquid charger and the sampling device 118. However, in the embodiment shown in FIG. 3, the connection mechanism comprises one or more rail elements 168, as an alternative or in addition to a hinge. The rail elements 168 are adapted to enable a relative movement of the liquid charger 116 and the sampling device. In this embodiment, a linear movement is enabled.

In FIG. 3, a cross-sectional view of one rail element 168 is shown. As can be seen, in this embodiment, the rail elements 186 comprise one or more guiding rods 170. Thus, as an example, two, three, four or more rail elements 168, preferably guiding rods 170, may be provided. In this embodiment, the guiding rods 170 are fixedly embedded in a first bore 172 in the sampling device 118, such as in a blind hole in a base plate 174 of the sampling device. Similarly, the liquid charger 116 may comprise a base plate 176 having a second bore 178, such as a through hole in the base plate 176, in which the guiding rod 170 is movably accommodated, such that the base plate 176 may glide over the guiding rod 170. As can be seen in FIG. 3, the guiding rod 170 may extend all the way through the base plate 176. On a side opposing the sampling device 118, the liquid charger 116 may comprise a cover plate 180, and the guiding rod 170 may be kept by a nut 182 or another type of fixing element, such that a relative movement of the base plate 176 along the guiding rod 170 is limited. The cover plate 180 may be locked to the base plate 176 by one or more fixing elements, such as one or more screws 184.

The connection mechanism 162 further may comprise one or more spring elements 186 adapted to apply a separating force separating the liquid charger 116 and the sampling device 118. In the embodiment shown in FIG. 3, the spring element 186 may comprise one or more coil springs surrounding the guiding rod 170, accommodated in a ring space of the bores 172, 178 and resting on shoulders 188, 190 of the bores 172, 178. The liquid charger 116 and the sampling device 118 may be compressed by using a tong 114 compressing these elements, whereby a relative movement of these elements 116, 118 defined by the rail element 168 is preformed and whereby a clamping force is applied to the biological sample 112. When the clamping force exerted by the tong 114 is reduced, the spring element 186 provides a force opposed to the clamping force, thereby opening the space in between the liquid charger 116 and the sampling device 118, in order to remove and/or replace the biological sample 112.

FIG. 3 further shows optional details of an embodiment of a supply system for supplying the extraction liquid 128 to the biological sample 112. In this embodiment, a liquid supply system 192 is shown, having a connection 194 to a liquid supply line 130, as in the preceding embodiments. Further, the liquid supply system 192 may comprise a valve housing 196 inserted in a valve receptacle 198 in the base plate 176. The valve housing 196 may comprise a rim 200 which may be clamped down by a spring 202 and the cover plate 180. However, other mechanisms for locking the valve housing 196 are possible. Further, the valve housing 196 in this embodiment comprises one or more valves, such as a back-pressure valve 204. In this embodiment, the back-pressure valve 204 comprises a ball 206 and a spring 208 and is adapted to prevent a back flow of the extraction liquid 128 into the supply line 130.

At a lower end facing the first surface 122 of the biological sample 112, the liquid charger 116, in this embodiment preferably the valve housing 196, may comprise a perforated plate 210 having one or more perforations providing the orifices 132 through which the extraction liquid may be supplied to the first surface 122 of the biological sample 112. The perforated plate 210 may be locked to the valve receptacle 198 by a screw connection or any other connection mechanism.

The embodiment shown in FIG. 3 further shows a potential modification of the sampling device 116. In this embodiment, a funnel 164 is provided in the base plate 174 of the sampling device 118. At an end facing the second surface 124 of the biological sample 112, the sampling device 118 again may have one or more filter elements 156. In the embodiment shown in FIG. 3, the filter element 156 may have a further perforated plate 212, which, again, may comprise one or more perforations and which preferably may be screwed into the base plate 118. Further, in between the perforated plate 212 and the second surface 124 of the biological sample 112, a mesh 214 or sieve may rest, providing a further filter element 156. Other embodiments are possible.

The embodiment in FIG. 3 further shows a modification of an accommodation of the sampling vessel 136. Thus, in the embodiment shown in FIG. 3, the sampling device 118 may comprise a holding plate 216 or any other holding element for the sampling vessel 136. In this embodiment, the holding plate 216 is located on the lower side of the base plate 174, i.e. on the side facing away from the biological sample 112. The holding plate 216 may be fixed to the base plate 174 or may be clamped to the base plate 174 by the tong 114. The holding plate 216 may comprise a shoulder 218 on which a rim 220 of the sampling vessel 136 may rest. Other types of receptacles holding the sampling vessel 136 are possible.

EXAMPLE OF AN EXTRACTION

In order to test an extraction process with the extraction device 110 according to the embodiment depicted in FIG. 3, the following experiment was performed.

Firstly, a corn leaf was clamped in between the liquid charger 116 and the sampling device 118 of the set-up shown in FIG. 3. In order to apply a clamping force, a tong 114 was applied as depicted in FIG. 3, wherein welding tongs were used.

In a further step, pressurized ethanol was applied as an extraction liquid 128. In order to pressurize the ethanol, a pressurizing element 148 (not depicted in FIG. 3) was used. In this case, a grease press was used as a pressurizing element 148.

As previously described, sample fluid 126 was collected in the sampling vessel 136. Even though a detailed analysis of the sample fluid 126 was not performed, the sample fluid 126 was visually inspected. A green coloration of the sample fluid 126 was easily detectable with the naked eye, without any further analysis, as opposed to the colorless ethanol used as the extraction liquid 128. This coloration of the sample fluid 126 clearly showed that at least one ingredient from the corn leaf was extracted, most likely chlorophyll, and, potentially, one or more other ingredients.

| Reference Numerals | |
|---|---|
| 110 | extraction device |
| 112 | biological sample |
| 114 | tong |
| 116 | liquid charger |
| 118 | sampling device |
| 120 | hinge |
| 122 | first side |
| 124 | second side |
| 126 | sample fluid |
| 128 | extraction liquid |
| 130 | liquid supply line |

| Reference Numerals | |
|---|---|
| 132 | orifice |
| 134 | first sealing element |
| 136 | sampling vessel |
| 138 | opening |
| 140 | second sealing element |
| 142 | receptacle |
| 144 | sample tempering element |
| 146 | extraction liquid tempering element |
| 148 | pressurizing element |
| 150 | pressure adjusting element |
| 152 | interior space |
| 154 | gas inlet |
| 156 | filter element |
| 158 | absorbing materials |
| 160 | reagent |
| 162 | connection mechanism |
| 164 | funnel |
| 166 | Port |
| 168 | rail element |
| 170 | guiding rod |
| 172 | first bore |
| 174 | base plate |
| 176 | base plate |
| 178 | second bore |
| 180 | cover plate |
| 182 | nut |
| 184 | screw |
| 186 | spring element |
| 188 | shoulder |
| 190 | shoulder |
| 192 | liquid supply system |
| 194 | connection |
| 196 | valve housing |
| 198 | valve receptacle |
| 200 | rim |
| 202 | spring |
| 204 | back-pressure valve |
| 206 | ball |
| 208 | spring |
| 210 | perforated plate |
| 212 | perforated plate |
| 214 | mesh |
| 216 | holding plate |
| 218 | shoulder |
| 220 | rim |

The invention claimed is:

1. A method for extracting at least one ingredient from a biological sample, comprising:
    a) contacting a liquid charger of an extraction device with a first side of a biological sample,
    b) applying an extraction liquid to the first side of the biological sample by using the liquid charger,
    c) contacting at least one sampling device of the extraction device with a second side of the biological sample,
    d) collecting a sample fluid comprising the extraction liquid and at least one ingredient by using the at least one sampling device,
    wherein the liquid charger comprises a pressurizing element which is adapted to provide the extraction liquid in a pressurized way,
    wherein the liquid charger has at least one first sealing element which is adapted to be pressed against the first side of the sample,
    wherein the exraction device has at least one second sealing element which is adapted to be pressed against the second side of the sample,
    wherein the liquid charger and the at least one sampling device are connected by at least one connection mechanism, wherein the at least one connection mechanism is adapted to vary a distance between the liquid charger and the at least one sampling device and wherein the liquid charger applies a clamping force to the biological sample located between the liquid charger and the at least one sampling device, wherein the biological sample is taken from a plant and is selected from the group consisting of leaves, trunks, stems, roots, storage roots, branches, inflorescences, flowers, infructescences, fruits, ears, cobs and seeds, wherein the extraction device is clamped onto the biological sample and the extraction is performed without cutting the plant into pieces.

2. The method according to claim 1, wherein the method is performed directly on plants grown in a field, a greenhouse or a growth chamber.

3. The method according to claim 1, wherein the biological sample is an intact part of a plant selected from the group consisting of: a plant growing in a controlled environment; a plant growing in soil or in a hydroponic system in a controlled environment; a plant growing in a field; a plant which belongs to a breeding population; and a transgenic plant.

4. The method according to claim 1, wherein the method is performed without separating the sample from the remaining biological entity.

5. The method according to claim 1, wherein the connection mechanism has at least one hinge.

6. The method according to claim 1, wherein the connection mechanism has at least one rail element enabling a relative movement of the liquid charger and the sampling device.

7. The method according to claim 6, wherein the rail element has at least one guiding rod.

8. The method according to claim 6, wherein the relative movement is a linear relative movement.

9. The method according to claim 1, wherein the connection mechanism has at least one spring element, wherein. the spring element is adapted to apply a separating force separating the liquid charger and the sampling device.

10. The method according to claim 1, wherein the extraction device is a hand-held device.

11. The method according to claim 1, wherein the sampling device has at least one sampling vessel, wherein the sampling device is adapted to at least partially guide the sample fluid into the sampling vessel.

12. The method according to claim 11, wherein the sampling vessel is arranged in the sampling device in a replaceable way.

13. The method according to claim 11, wherein the sampling device has at least one pressure adjusting element adapted to adjust a gas pressure inside the sampling vessel.

14. The method according to claim 11, wherein the sampling device has at least one gas inlet adapted to expose at least one interior space of the sampling vessel with gas.

15. The method according to claim 1, wherein the sampling device has at least one sample tempering element, wherein the sample tempering element is adapted to temper the sample fluid.

16. The method according to claim 1, wherein the sampling device has at least one funnel for receiving the sample fluid.

17. The method according to claim 1, wherein the extraction device has at least one filter element for filtering the sample fluid.

18. The method according to claim 17, wherein the filter element is selected from the group consisting of: a mesh, a screen, a sieve, a grill, and a perforated plate having one or more. perforations.

19. The method according to claim 1, wherein the liquid charger has at least one pressurizing element, wherein the pressurizing element is adapted to provide the extraction liquid in a pressurized way.

20. The method according to claim 1, wherein the extraction device has at least one valve.

21. The method. according to claim 20, wherein the liquid charger has the at least one valve.

22. The method according to claim 20, wherein the valve is a back-pressure valve.

23. The method according to claim 1, wherein the liquid charger has at least one extraction liquid tempering element, wherein the extraction liquid tempering element is adapted to temper the extraction liquid.

24. The method according to claim 1, wherein the sampling device has at least one absorbing material adapted for absorbing the ingredient.

25. The method according, to claim 24, wherein the absorbing material is adapted for one of an enrichment and a depletion of the ingredient.

26. The method according to claim 1, wherein the extraction liquid is supplied from the liquid charger via a liquid supply line to the first side of the biological sample.

27. The method according to claim 1, wherein an external component is used to apply the clamping force.

28. An extraction system, comprising at least one extraction device for extracting at least one ingredient from a biological sample, the extraction device having at least one liquid charger, wherein the liquid charger is adapted to be brought in contact with a first side of the sample and wherein the liquid charger is adapted to apply an extraction liquid to the first side of the sample, the extraction device further having at least one sampling device, wherein the sampling device is adapted to he brought in contact with a second side of the sample and wherein the sampling device is adapted to collect sample fluid comprising the extraction liquid and the ingredient, the extraction system further comprising at least one biological sample, wherein the biological sample is clamped between the liquid charger and the sampling device, wherein the liquid charger and the sampling device are connected by at least one connection mechanism, wherein the connection mechanism is adapted to vary a distance between the liquid charger and the sampling device and wherein the liquid charger applies a clamping three to the sample located between the liquid charger and the sampling device, wherein the liquid charger comprises a pressurizing element which is adapted to provide the extraction liquid in a pressuried way, wherein the liquid charger has at least one first sealing element which is adapted to be pressed against the first side of the sample, wherein the extraction device has at least one second sealing element which is adapted to be pressed against the second side of the sample wherein the biological sample is taken from a plant and is selected from the group consisting of leaves, trunks, stems, roots, storage roots, branches, inflorescences, flowers, infructescences, fruits, ears, cobs and seeds, wherein the extraction device is clamped onto the biological sample for performing the extraction without cutting the plant into pieces.

* * * * *